United States Patent [19]

Fleury

[11] Patent Number: 5,368,583
[45] Date of Patent: Nov. 29, 1994

[54] BODILY FLUID TEST KIT

[75] Inventor: Richard Fleury, Orland Park, Ill.

[73] Assignee: GKR Industries, Inc., Chicago, Ill.

[21] Appl. No.: 101,209

[22] Filed: Aug. 3, 1993

[51] Int. Cl.⁵ .............................................. A61M 1/00
[52] U.S. Cl. .................................... 604/318; 604/322;
604/323; 604/346; 604/347; 604/349; 128/760;
128/767; 128/771
[58] Field of Search ...................... 4/144.1–144.4;
128/760–761, 763, 766, 767, 771; 604/317–318,
321, 322–324, 346–347, 349–350, 408–409, 403,
404

[56] References Cited

U.S. PATENT DOCUMENTS

| | | | |
|---|---|---|---|
| 3,346,883 | 10/1967 | Ersek | 4/144.2 |
| 3,403,410 | 10/1968 | Benzel et al. | 4/144.2 |
| 4,990,145 | 2/1991 | Fleury | 604/317 |
| 5,065,459 | 11/1991 | Tjahaja et al. | 4/144.3 |
| 5,176,665 | 1/1993 | Watanabe et al. | 604/332 |
| 5,282,683 | 2/1994 | Brett | 128/771 |

FOREIGN PATENT DOCUMENTS

| | | | |
|---|---|---|---|
| 2819574 | 11/1978 | Germany | 128/767 |
| 0225337 | 7/1985 | Germany | 604/318 |
| 9008525 | 8/1990 | WIPO | 4/144.3 |
| 9200048 | 1/1992 | WIPO | 604/349 |

Primary Examiner—Randall L. Green
Assistant Examiner—P. Zuttarelli
Attorney, Agent, or Firm—Baker & McKenzie

[57] ABSTRACT

An improved disposable container is provided for the collection and testing of bodily fluid samples, such as urine specimens. The improved container includes a collection bag sealably attached to a tubular member equipped with a lower valve means. A protective sleeve surrounds the collection bag and protects both the patient's hands as well as the medical technician's hands during transport and handling of the container once the specimen is deposited therein. The tubular member preferably includes an upper closure means with an access hole disposed therein. After the specimen is disposed through the tubular member and into the collection bag, the closure means disposed on top of the tubular member is closed and a test strip is deposited through the access means. Then, the sleeve is flipped upward and the open end of the sleeve is closed or sealed thereby closing the disposable container and sealably containing the specimen therein. The test strip and specimen may then be examined through the clear collection bag.

15 Claims, 2 Drawing Sheets

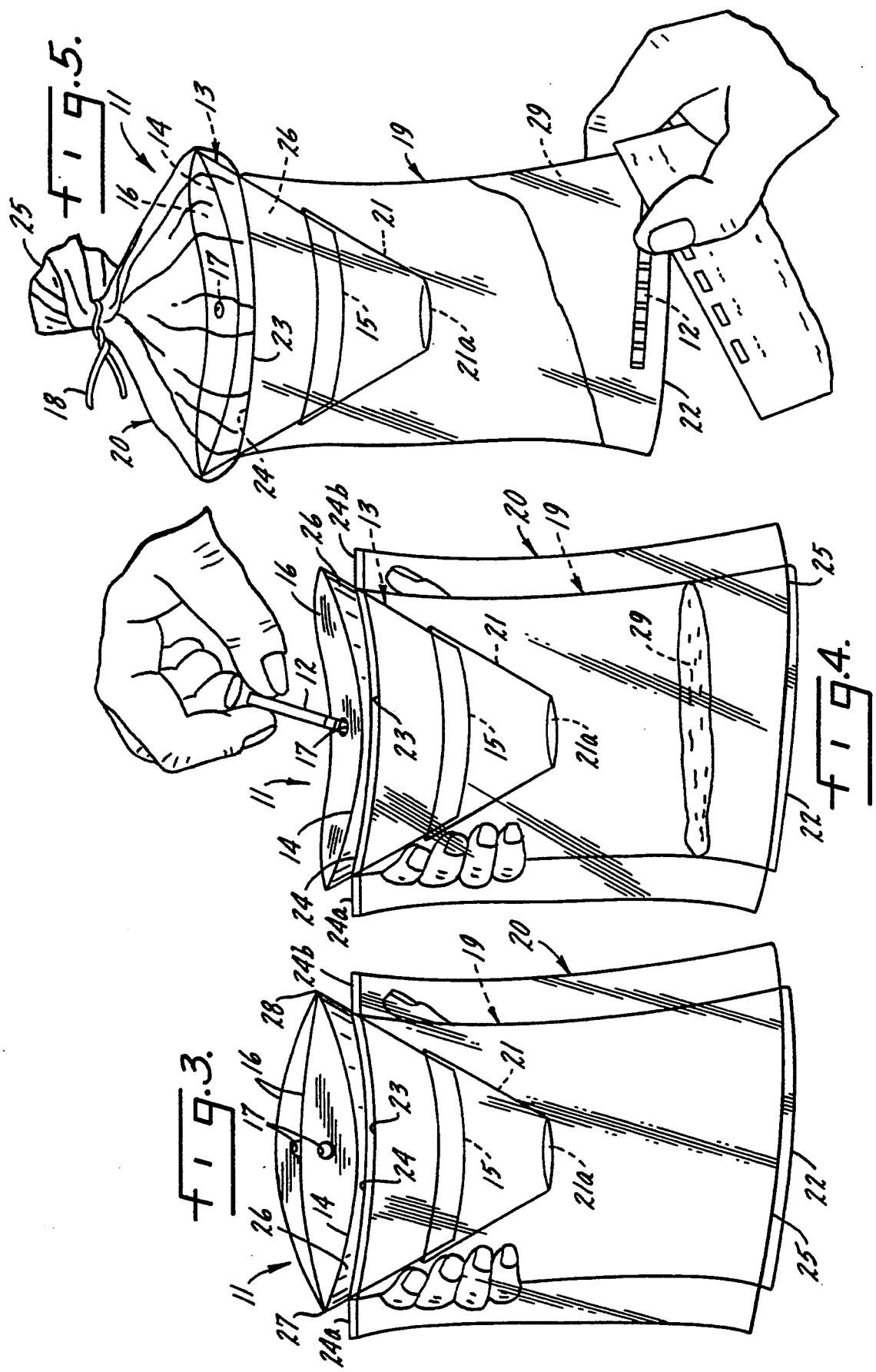

BODILY FLUID TEST KIT

FIELD OF THE INVENTION

This invention relates generally to a kit including a disposable container for accepting bodily fluid specimens and a test strip for testing said specimens. More specifically, the invention relates to a disposable specimen container which includes a valved tubular member through which bodily fluid flows into a collection bag. An outer protective sleeve protects the user's hand against contact with the bodily fluid. The upper end of the tubular member is closable but includes a means for inserting a test strip into the collection bag after closing. The sleeve folds upward and is sealable to provide safe transport of the bodily fluid specimens.

BACKGROUND OF THE INVENTION

The concept of disposable containers for the collection of bodily fluid specimens such as urine specimens is well known. The most common form of such a container is a plastic or paper cup. Most of such cup-type disposable containers include some sort of closure lid. The disadvantages to cup-type containers for the collection of specimens are at least three-fold. First, the cups are rather small in volume with relatively small openings, and patients, especially women, sometimes find it difficult to deposit a bodily fluid specimen such as urine in the cup without spillage or overflow. Second, once the fluid is deposited in the container, the fluid is sometimes spilled in the process of being delivered to a nurse or technician for testing Third, there is no easy way to deposit a test strip in the fluid so that it can be visually inspected in the fluid. Placing a test strip in the fluid requires that the lid of the container be removed, and this requirement enhances the likelihood of the specimen being spilled and coming into contact with the nurse or technician.

U.S. Pat. Nos. 3,797,734 and 4,990,145 show a disposable bag of the type with which the present invention is intended to be used. Specifically, the '734 patent shows a bag having a tubular funnel sealingly engaging a plastic bag. The bag is sealably attached to the outer surface of the tubular member. The lower end of the tubular member includes a funnel means comprised of a flattenable plastic tube which allows entry of the fluid through the tubular member into the bag, but which prevents fluid from escaping upward and reentering the tubular member. The '145 patent provides an improvement to the embodiment disclosed in the '734 patent by means of a protective outer sleeve or shroud for protecting the user's skin against fluid contact. As noted in the '145 patent, products made in accordance with both patents have been sold in substantial numbers.

It is imperative that nurses and other medical personnel avoid contact with the bodily fluids of their patients. Hepatitis B virus, HIV (human immunodeficiency virus) and other diseases may be transmitted as a result of contact with bodily fluids. Further, the Occupational Safety and Health Administration (OSHA) has issued regulations covering medical employees that medical practices must comply with (see 29 C.F.R. § 1910.1030 et seq.).

Thus, there is a need for a disposable specimen container that is easy to use and protects both the patient and medical technician against coming in contact with the bodily fluids. Second, there is a need for a disposable specimen container that may be transported or handed from the patient to a technician without the risk of spillage, either on the patient or on the technician. Third, there is a need for a disposable specimen container that facilitates the insertion of a test strip into the fluid and further facilitates the viewing of the test strip while it is in the fluid without requiring the technician to reach down into the container to retrieve the test strip for inspection.

As discussed below, the present invention satisfies all three of the aforenoted criteria.

SUMMARY OF THE PRESENT INVENTION

The present invention makes a significant contribution to the disposable medical container art by providing an improved disposable container for accepting and transporting bodily fluids, including urine. The invention features a tubular member with a valve means attached to the lower end of the tubular member. A collection bag is sealably attached to an outer surface of the tubular member. The closed bottom end of the collection bag provides a space for the collection of fluid and the valve means provides a means for containing the fluid in the collection bag and preventing it from spilling upward through the tubular member. An optional sleeve may be sealably attached to the outer surface of the tubular member at or slightly above the area where the collection bag is sealably attached to the tubular member. During initial use of the container by the patient, the sleeve is folded downward and provides a skirt for the collection bag. Holes in the closure means disposed at the top of the tubular member allow the container to hang from a peg in the examination room or bathroom stall. The peg may be supplied as part of the kit.

After the patient has completed depositing fluid in the collection bag, the patient then hands the container to a nurse or technician who, if a sleeve is employed, will slip his/her hand up under the sleeve between the sleeve and the collection bag thereby grasping the container and protecting the nurse or technician's hand from contact with the bodily fluid. As discussed above, in the preferred embodiment, the upper end of the tubular member will include a closure means such as a lid or closure flaps to further preclude any spillage or splatter of bodily fluid during the transfer between the patient and the nurse or technician. Also in the preferred embodiment, the closure means includes an access hole which enables the nurse or technician to easily insert a test strip down into the collection bag and into the bodily fluid for examination and testing of the fluid. The access hole, as noted above, also provides the bag with means for hanging the bag from a peg before or after use by the patient.

After the test strip has been inserted into the fluid, the sleeve may be folded upward over the upper end of the tubular member and the distal end of the sleeve may be sealed with a twist-tie or other equivalent sealing means. The distal end of the sleeve may also include a built-in sealing mechanism. After the distal end of the sleeve is sealed, the disposable container, the fluid and the test strip may be safely transported without fear of spilling the fluid. After the test strip has been examined, the entire container, including the fluid and the test strip may be safely disposed of.

Female patients find the preferred embodiment of the present invention far superior to a cup or cylindrical container because the configuration of the present invention is designed to be easily used by women without spillage. Male patients also find the preferred embodiment of the present invention easier to use because it prevents overflow.

The preferred embodiment features a conical or funnel-shaped tubular member with a wider upper end for easy use by the patient. The narrow lower end of the tubular member effectively deposits the fluid into the center of the collection bag and also provides additional room so that the patient and nurse or technician may easily slide his/her hand between the collection bag and the sleeve to grasp the upper portion of the collection bag and the tubular member.

The present invention also lends itself to an improved method for depositing bodily fluids into a disposable container. The method includes the patient taking a disposable container made in accordance with the present invention which may or may not have been hung from a peg and opening the closure means that is disposed at the upper end of the tubular member. After the closure means is opened, the patient then deposits the fluid sample down through the tubular member and through the valve means and into the collection bag. After the patient has completed depositing fluid in the bag, the container may be hung on a wall by inserting a wall mounted peg through the access means. The patient then removes the container from the peg and closes the closure means disposed at the upper end of the tubular member. The patient then hands the disposable container to a nurse or technician who takes the container by inserting his/her hand upward between the collection bag and the outer sleeve to grasp the tubular member. The nurse or technician then inserts a test strip downward through an access means disposed in the closure means of the tubular member. The test strip falls through the tubular member and into the fluid now disposed in the collection bag. The technician then pulls the outer sleeve upward and sealably closes the distal end of the protective sleeve with a twist-tie or other sealing mechanism that may or may not be built in to distal end of the protective sleeve.

It is therefore an object of the present invention to provide an improved disposable container for accepting and transporting bodily fluid samples.

It is another object of the present invention to provide and improved disposable container for bodily fluid samples that reduces the likelihood of any spillage of the bodily fluid samples thereby reducing the likelihood of the patient or technician coming into contact with the fluid.

Yet another object of the present invention is to provide a disposable bodily fluid specimen bag that effectively prevents the possibility of a nurse or medical technician contacting HBV (hepatitis B virus), HIV (human immunodeficiency virus) and further helps medical practices to comply with the relevant OSHA regulations (37 C.F.R.§1910.1030 et seq.).

Still another object of the present invention is an improved device for the collection of urine specimens from female and male patients.

Yet another object of the present invention is to provide an improved disposable container for bodily fluid specimens that facilitates the safe transport and testing of fluid specimens.

BRIEF DESCRIPTION OF THE DRAWINGS

This invention is illustrated more or less diagrammatically in the accompanying drawings, wherein:

FIG. 3 is a front elevational view of the disposable container shown in FIG. 1 as held by a user or medical technician;

FIG. 4 is a front elevational view of the disposable container shown in FIG. 3 after the deposit of a specimen therein and further illustrating the insertion of a test strip downward into the container; and FIG. 5 is yet another front elevational view of the disposable container shown in FIG. 3 with the outer protective sleeve folded upward and sealed and further illustrating the easy examination of the test strip, now contained within the fluid sample.

Figure 1:
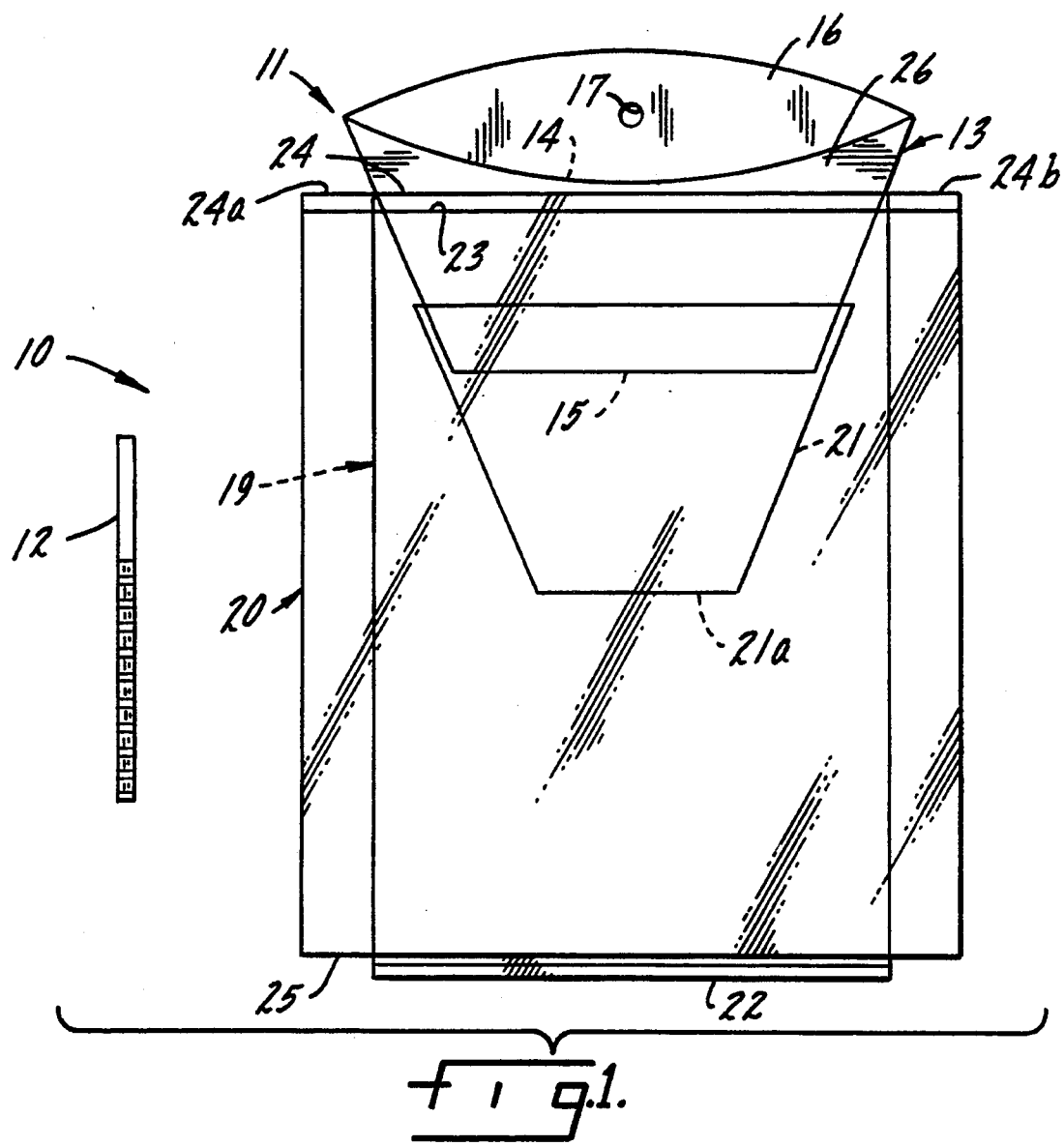
FIG. 1 is a front elevational view of a disposable container kit made in accordance with the present invention.

It should be understood that the drawings are not necessarily to scale and details which are not necessary for an understanding of the present invention or which render other details difficult to perceive may have been omitted. It should also be understood, of course, that the invention is not necessarily limited to the particular embodiment illustrated herein.

DETAILED DESCRIPTION OF THE INVENTION

Like reference numerals will be used to refer to like or similar parts from figure to figure in the following description of the drawings.

The dramatic improvement contributed by the present invention is best understood after consideration of how convention specimen containers are used. First, conventional specimen containers are merely paper or plastic cups with an open top end. While a wide top is preferable for the insertion of the bodily fluid in the container by the patient, it also enables the fluid to easily spill out of the container. Further, many patients, especially female patients, find that the size or width of the upper end of the containers now in use is too small and that the fluid is often spilled during the deposit of the fluid in the container. Male patients find the volume of the cup-type containers too small and often overfill them or spill the contents after the deposit is made. Finally, after fluid is deposited in the container, the fluid may be spilled before a lid is placed on the container and the lid must be removed afterward prior to the insertion of a test strip or the removal of a portion of the fluid specimen for testing.

As seen below, the present invention overcomes all these disadvantages by providing a disposable container with a wide open end to facilitate the deposit of fluid in the container and with at least two features that help protect against spillage of the fluid during and after deposit of the fluid in the container. The present invention also makes it safe and easy to deposit of a test strip in the fluid and further facilitates the examination of the test strip once deposited therein.

FIG. 1 is an illustration of a kit 10 which may include a disposable container 11 as well as a test strip 12 and a peg for hanging the container 11 on an examination room wall or in a bathroom stall (the peg is not shown). The container 11 includes the following components. A tubular member, shown generally at 13 is preferably funnel or conical shaped. The upper end 14 is preferably wider than the lower end 15 which makes it easier for a patient to deposit bodily fluids in the upper end 14 of the tubular member 13. The lower end 15 of tubular member 13 is sealably attached to valve means 21. The lower end 21a of the valve means 21 allows fluid to flow downward through the valve means 21 to the lower end 22 of the collection bag 19 but does not allow liquid to exit the bag 19. Also illustrated in FIG. 1 is the closure means 16 which, in the case of the embodiment shown in FIG. 1, includes a flap 16 attached to the upper end 14 of the tubular member 13. The aperture 17 provides a means for inserting the test strip 12 after fluid is deposited in the container 11 and after the closure means or lid 16 is shut. The aperture or access means 17 may also be used to hang the container 11 from a peg or hook (not shown).

Still referring to FIG. 1, the container 11 of the present invention includes a collection bag 19 and a sleeve 20. The collection bag 19 includes a lower closed end 22 which serves as the receptacle for the fluid sample. The upper open end 23 of the collection bag 19 is sealably attached to the outer surface or outer periphery 26 of the tubular member 13.

The outer sleeve 20 is disposed around the collection bag 19. Both the upper end 24 and the lower end 25 of the sleeve 20 are initially open. The upper end 24 is sealably attached to the outer surface 26 of the tubular member 13 at or slightly above the point where the upper end 23 of the collection bag 19 is sealably attached to the outer surface 26 of the tubular member. The upper outer edges 24a and 24b are sealed to form a closed sleeve around the collection bag 19 and to prevent any fluid from entering the sleeve through the upper end 24 and further to prevent fluid from coming into contact with the patient's hand. The lower end 25 of the sleeve 20 remains open to facilitate the insertion of a hand up through the lower end 25 and between the lower end 25 of the sleeve 20 and the lower end 22 of the collection bag 19.

Figure 2:
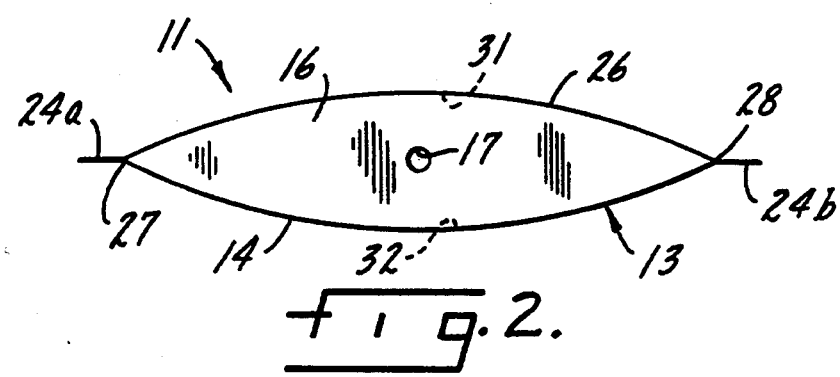
FIG. 2 is a top plan view of the disposable container shown in FIG. 1.

FIG. 2 presents a top view of the disposable collection bag initially shown in FIG. 1. The closure means or closure flap 16 has been flipped downward to cover the upper end 14 of the tubular member 13. It will be noted that the tubular member 13 is made of flexible material such as plastic or cardboard arid the distal ends 27, 28 are squeezed inward toward each other to widen the surface area of the upper end 14 (see also FIG. 1) of the tubular member 13. Upon release of the ends 27, 28, the opposing side walls 31, 32 move toward each other and the distal ends 27, 28 move away from each other to partially close the upper end 14 of the tubular member and the valve means 21 which precludes spillage of the liquid specimen. The position of the container 11 shown in FIG. 2 is illustrative of the position of the container 11 after a fluid sample has been deposited in the collection bag 19. The patient has closed the flap 16 and hands the container 11 to the nurse. The flap 16 includes the aperture or access means 17 so as to facilitate the insertion of a test strip 12 (see FIG. 1) through the closure means or flap 16 and through the valve means 21 and down into the fluid as discussed below.

FIG. 3 is an illustration of the container 11 prior to use by a patient. The patient grasps the collection bag 19 between the collection bag 19 and the sleeve 20 up towards the upper end 23 of the collection bag 19 and around the tubular member 13. As discussed above with respect to FIG. 2, squeezing the distal ends 27, 28 of the tubular member 13 together widens the upper end 14 of the tubular member and makes the container 11 easier to use.

After depositing fluid 29 through the tubular member 13 and valve means 21 and down towards the lower end 22 of the collection bag 19, the patient then flips the two closure flaps 16 downward to close the upper end 14 of the tubular member 13. Before closing the flaps 16, the container 11 may be hung by the hole 17 on a hook or peg while the patient gets dressed. After taking the container 11 from the patient or removing the container 11 from a peg or hook, the nurse or technician inserts a test strip 12 down through the access holes 17 disposed in the flaps or closure means 16.

As seen in FIG. 5, the test strip 12 may be easily examined through the clear collection bag 19. After the test strip 12 is inserted through the access holes 17, the nurse or technician grasps the lower end 25 of the sleeve 20 and pulls it upward above the upper end 14 of the tubular member 13. The now-upper end 25 of the sleeve 20 may be sealed with a wire-type twist-tie 18 or another sealing means may be employed. For example, the end 25 of the sleeve 20 may be equipped with a built-in sealing means such a plastic zipper lock or other equivalent sealing means.

The container 11 shown in FIG. 5 is leak proof due to the multiple seal provided by the valve means 21 and the sealable attachment of the upper end 23 of the collection bag 19 to the outer surface 26 of the tubular member 13 and the sealable attachment of the end 24 of the sleeve 20 to the outer surface 26 of the tubular member 13. As seen in FIG. 5, the container may be placed on a counter top without fear of leakage. After the examination of the test strip 12 is completed, the entire container 11 as shown in FIG. 5 is thrown away.

From the above description of the preferred embodiment, it is apparent that the objects of the present invention have been achieved. While only one embodiment has been set forth, alternative embodiments and various modifications will be apparent from the above description to those skilled in the art. For example, the shape of the tubular member 13 may be modified to be more funnel-shaped or more cylindrically-shaped. Further, the collection bag 19 and sleeve 20 may be fabricated from a single piece of plastic and attached to the outer surface or outer periphery 26 of the tubular member 13. As noted above, the end 25 of the sleeve 20 may be equipped with a self-sealing means or a zipper-type closure along the end 25 of the sleeve. Such closures are disclosed in U.S. Pat. Nos. 4,601,694 to Ausnit, 3,980,225 to Kan and 4,055,109 to Kan. It will also be noted that the test strip or test means may be pre-attached to the interior of the collection bag. These and other alternatives ere considered equivalents and within the spirit and scope of the present invention.

Accordingly, it is intended that the scope of the invention be limited solely by the scope of the hereafter appended claims and not by any specific wording in the foregoing description.

I claim:

1. A kit for collecting and testing bodily fluids, the kit comprising:
 a disposable container including
  a tubular member having an upper end portion and a lower end portion, the upper end portion including a closure means and with an access hole disposed therein,
  valve means sealably attached to the lower end portion of the tubular member, a collection bag, the bag including an upper portion that is sealably attached to an outer surface of the tubular member, a sleeve including a first open end portion and a second open end portion, the first open po- rion being sealably attached to the outer surface of the tubular member between an upper end of the tubular member and the upper portion of the collection bag, the second open end portion of the sleeve folding upward over the upper end of the tubular member and being sealable the upper portion of the collection bag, which is sealably attached to the tubular member, in combination with the valve means and the second open end portion of the sleeve providing substantial containment of fluid within the disposable container after fluid is disposed therein;

a test strip having dimensions small enough to fit through the access hole of the closure means so the test strip may be deposited into fluid contained in the collection bag after deposit of fluid therein.

2. The kit of claim 1,
further comprising a peg means for mounting on a wall, the peg means accommodating the access hole in the closure means enabling the container to be temporarily suspended from the peg means.

3. The kit of claim 2,
wherein the tubular member is generally conically-shaped.

4. The kit of claim 3,
wherein the closure means includes two overlapping opposing flaps attached to the upper end of the tubular member, each flap folding inward, one on top of the other, to substantially close the upper end of the tubular member.

5. The kit of claim 4,
wherein each flap includes an access hole, the two access holes of the flaps overlapping when the flaps are folded inward, the two overlapping access holes providing access to the tubular member and collection bag when the upper end of the tubular member is closed by the flaps.

6. The kit of claim 5,
wherein the collection bag is made from clear, flexible plastic.

7. The kit of claim 6,
wherein the sleeve is made from clear, flexible plastic.

8. A disposable container for accepting bodily fluid samples, the container comprising:

a conically-shaped tubular member including an upper end and a lower end, the upper end of the conically-shaped tubular member being of a larger diameter than the lower end of the conically-shaped tubular member, the upper end of the conically-shaped tubular member being further characterized as including closure means to preclude spillage of bodily fluid out the upper end of the conically-shaped tubular member after passage of bodily fluid through the conically-shaped tubular member to a collection bag, the closure means including an access hole providing access to the collection bag by a test strip after closure of the conically-shaped tubular member, the access hole also providing means for hanging the container from a hook or peg, valve means being sealably attached to the lower end of the conically-shaped tubular member, the collection bag including a upper portion providing an opening for the bag, the upper portion of the collection bag being sealably attached to the outer surface of the conically-shaped tubular member between the upper and lower ends thereof, a sleeve including a first open end portion and a second open end portion, the first open end portion being sealably attached to the outer surface of the conically-shaped tubular member between the upper end of the conically-shaped tubular member and the upper portion of the collection bag, the second open end portion including a sealable closure, the sleeve being disposed around the collection bag and the second open end portion of the sleeve being disposed near the closed lower portion of the collection bag during the deposit of fluid into the collection bag, the second open end portion of the sleeve folding upward over the upper end of the conically-shaped tubular member and being closable, the upper portion of the collection bag which is sealably attached to the outer portion surface of the conically-shaped tubular member and the first end portion of the sleeve that is sealably attached to the conically-shaped tubular member in combination with the valve means and said sealable closure of the second open end portion of the sleeve substantially containing fluid in the disposable container after deposit of fluid therein.

9. The container of claim 8,
wherein the closure means includes two overlapping opposing flaps attached to the upper end of the conically-shaped tubular member, each flap folding inward, one on top of the other, to substantially close the upper end of the conically-shaped tubular member.

10. The container of claim 9,
wherein each flap includes a hole, the two holes of the flaps overlapping when the flaps are folded inward, the two overlapping holes providing access to the conically-shaped tubular member and collection bag when the conically-shaped tubular member is closed by the flaps thereby enabling the insertion of a test strip downward into the collection bag after closure of the conically-shaped tubular member with the flaps.

11. The container of claim 10,
wherein the collection bag and sleeve are made from clear, flexible plastic.

12. The container of claim 11,
wherein the second open end portion of the sleeve includes sealing means for providing a water-tight seal for containing bodily fluids in the kit.

13. A method of depositing a bodily fluids into disposable container and examination and testing said fluids, the method comprising:

depositing bodily fluid into a disposable container, the container including a conically-shaped tubular member including an upper end and a lower end, the upper end of the conically-shaped tubular member being of a larger diameter than the lower end of the conically-shaped tubular member, the upper end of the conically-shaped tubular member being further characterized as including lid means to substantially close the upper end of the conically-shaped tubular member, the lid means including at least one hole for the insertion of a testing device, the conically-shaped tubular member including an outer surface, valve means being sealably attached to the lower end of the conically-shaped tubular member, a collection bag, the bag including a upper portion providing an opening for the bag, the upper portion of the collection bag being sealably attached to the outer surface of the conically-shaped tubular member between the upper and lower ends thereof, a sleeve including a first open end portion and a second open end portion, the first open end portion being sealably attached to the outer surface of the conically-shaped tubular member between the upper end of the conically-shaped tubular member and the upper portion of the collection bag, the sleeve being disposed around the collection bag and the second open end portion of the sleeve being disposed near the closed lower portion of the collection bag during the deposit of fluid into the collection bag, closing the lid means of the conically-shaped tubular member, inserting the testing device through the hole in the lid means thereby causing the testing device to drop downward into contact with the bodily fluid, folding the second open end portion of the sleeve upward over the conically-shaped tubular member and sealing the second open end portion of the sleeve, visually examining the testing device through the collection bag.

14. A disposable container for collecting, containing, isolating and testing bodily fluids, the container comprising:

a tubular member having an upper end portion and a lower end portion, the upper end portion including a closure and with an access hole disposed therein, a valve sealably attached to the lower end portion of the tubular member, a collection bag, the bag including an upper portion that is sealably attached to an outer surface of the tubular member, a sleeve including a first open end portion and a second open end portion, the first open end portion being sealably attached to the outer surface of the tubular member between an upper end of the tubular member and the upper portion of the collection bag, the second open end portion of the sleeve folding upward over the upper end of the tubular member and being sealable, the upper portion of the collection bag, the valve and the second open end of the sleeve combining to provide substantial containment of fluid within the disposable container after fluid is disposed therein.

15. A kit for collecting and testing bodily fluids, the kit comprising:

a disposable container including a tubular member having an upper end portion and a lower end portion, the upper end portion including a closure and with an access hole disposed therein, a valve sealably attached to the lower end portion of the tubular member, a collection bag, the bag including an upper portion that is sealably attached to an outer surface of the tubular member, a sleeve including a first open end portion and a second open end portion, the first open end porion being sealably attached to the outer surface of the tubular member between an upper end of the tubular member and the upper portion of the collection bag, the second open end portion of the sleeve folding upward over the upper end of the tubular member and being sealable, the upper portion of the collection bag, the valve and the second open end of the sleeve combining to provide substantial containment of fluid within the disposable container after fluid is disposed therein;

a test strip having dimensions small enough to fit through the access hole of the closure so the test strip may be deposited into fluid contained in the collection bag after deposit of fluid therein.

* * * * *